US010981102B2

(12) United States Patent
Trent et al.

(10) Patent No.: US 10,981,102 B2
(45) Date of Patent: Apr. 20, 2021

(54) AIRCRAFT AIR PURIFICATION AND VOLATILE ORGANIC COMPOUNDS REDUCTION UNIT

(71) Applicant: The Boeing Company, Chicago, IL (US)

(72) Inventors: Stephen M. Trent, Everett, WA (US); David R. Space, Everett, WA (US); Rajesh Talwar, Frontenac, MO (US); Hülya Cebeci, Istanbul (TR)

(73) Assignee: The Boeing Company, Chicago, IL (US)

( * ) Notice: Subject to any disclaimer, the term of this patent is extended or adjusted under 35 U.S.C. 154(b) by 282 days.

(21) Appl. No.: 16/163,051

(22) Filed: Oct. 17, 2018

(65) Prior Publication Data

US 2020/0122078 A1 Apr. 23, 2020

(51) Int. Cl.
*A61L 9/20* (2006.01)
*B64D 13/06* (2006.01)
(Continued)

(52) U.S. Cl.
CPC ............ *B01D 53/007* (2013.01); *A61L 9/205* (2013.01); *B01D 53/869* (2013.01);
(Continued)

(58) Field of Classification Search
None
See application file for complete search history.

(56) References Cited

U.S. PATENT DOCUMENTS

2015/0064061 A1  3/2015  Taghipour
2015/0359922 A1* 12/2015  Kim .................... A61L 9/00
                                                    422/121
(Continued)

FOREIGN PATENT DOCUMENTS

CN  101371929 A    2/2009
CN  102985116 A *  3/2013  ............ B01J 21/063
(Continued)

OTHER PUBLICATIONS

English machine translation for CN 107308483 A. Retrieved from EPO website on Sep. 28, 2020. (Year: 2020).*
(Continued)

*Primary Examiner* — Jennifer A Leung
(74) *Attorney, Agent, or Firm* — Coats & Bennett, PLLC

(57) ABSTRACT

A compact, lightweight, low power aircraft air filtration and VOC removal unit enables the removal of VOCs from cabin air in a passenger aircraft. A plurality of baffles having air flow-through airflow spaces are spaced apart along a duct. UV LEDs are mounted on the interior sides of the outermost baffles, and on both sides of all interior baffles. A filter module is disposed between pairs of baffles, and spaced from the baffles sufficiently to illuminate the entirety of both sides. Each filter modules comprises a plurality of filters. The filters are selected from a coarse foam, a fine foam, or a fused quartz filament felt. Each filter is loaded with a catalyst including one or more of AEROXIDE® P25, other pure titanium dioxide ($TiO_2$), iron-doped $TiO_2$, carbon-doped $TiO_2$, and combinations thereof. The catalysts on the filters, under UV illumination, chemically reduce VOCs in the airflow to non-VOC molecules.

20 Claims, 4 Drawing Sheets

(51) Int. Cl.
*B01D 53/86* (2006.01)
*B01D 53/88* (2006.01)
*B01D 53/00* (2006.01)
*B01J 21/06* (2006.01)
*B01J 21/18* (2006.01)
*B01J 23/745* (2006.01)
*B01J 35/00* (2006.01)
*B01J 35/04* (2006.01)

(52) U.S. Cl.
CPC ....... *B01D 53/8687* (2013.01); *B01D 53/885* (2013.01); *B01J 21/063* (2013.01); *B01J 21/18* (2013.01); *B01J 23/745* (2013.01); *B01J 35/004* (2013.01); *B01J 35/04* (2013.01); *B64D 13/06* (2013.01); *B01D 2255/20707* (2013.01); *B01D 2255/20738* (2013.01); *B01D 2255/702* (2013.01); *B01D 2255/802* (2013.01); *B01D 2257/708* (2013.01); *B01D 2258/06* (2013.01); *B01D 2259/804* (2013.01); *B64D 2013/0651* (2013.01)

(56) References Cited

U.S. PATENT DOCUMENTS

2016/0256590 A1* 9/2016 Taghipour ............... A61L 9/205
2020/0268927 A1* 8/2020 Asano ...................... A61L 9/00

FOREIGN PATENT DOCUMENTS

| CN | 107308483 A | * | 11/2017 |
| DE | 102005010012 A1 | | 11/2005 |
| EP | 2959921 A1 | | 12/2015 |
| EP | 1697045 B1 | | 8/2018 |

OTHER PUBLICATIONS

English machine translation for CN 102985116 A. Retrieved from EPO website on Sep. 28, 2020 and Sep. 29, 2020 (Year: 2020).*

* cited by examiner

AIRCRAFT AIR PURIFICATION AND VOLATILE ORGANIC COMPOUNDS REDUCTION UNIT

TECHNICAL FIELD

The present disclosure relates generally to aircraft, and in particular to a system and method for the removal of Volatile Organic Compounds (VOC) in an aircraft.

BACKGROUND

Volatile organic compounds (VOC) are a class of organic chemicals characterized by a high vapor pressure at room temperature, typically resulting from a low boiling point. They include non-methane hydrocarbons (NMHC) and oxygenated NMHC (e.g., alcohols, aldehydes and organic acids). VOCs emanate from off-gassing of foams, plastics, fabrics, and other manufactured products, particularly when they are new, and from the solvents in many cleaning products. VOCs are also produced as byproducts of human metabolic processes. Over 200 VOCs have been identified in human alveolar breath. In a closed environment full of people, such as a passenger aircraft, endogenously produced VOCs dominate.

From measurement campaigns, the primary complaints from passengers and crew in the aircraft are eye, nasal tract and throat irritation. Industry (FAA CoE ACER, ASHRAE) research has shown that many of these complaints are sourced from gaseous contaminants, notably VOCs.

VOCs cannot be removed by typical air filtration methods such as HEPA filtration. Existing systems to reduce VOC concentration in the cabin environment include activated carbon.

The Background section of this document is provided to place aspects of the present disclosure in technological and operational context, to assist those of skill in the art in understanding their scope and utility. Unless explicitly identified as such, no statement herein is admitted to be prior art merely by its inclusion in the Background section.

SUMMARY

The following presents a simplified summary of the disclosure in order to provide a basic understanding to those of skill in the art. This summary is not an extensive overview of the disclosure and is not intended to identify key/critical elements of aspects of the disclosure or to delineate the scope of the disclosure. The sole purpose of this summary is to present some concepts disclosed herein in a simplified form as a prelude to the more detailed description that is presented later.

According to one or more aspects of the present disclosure described and claimed herein, a compact, lightweight, low power aircraft air filtration and VOC removal unit enables the removal of VOCs from cabin air in, e.g., a passenger aircraft. Cabin air is directed through a duct. Transverse to a longitudinal axis of the duct, a plurality of baffles having air flow-through airflow spaces are spaced apart along the axis. Ultraviolet (UV) LEDs are mounted on the interior sides of the outermost baffles, and on both sides of all interior baffles. A filter module is disposed between pairs of baffles, transverse to the longitudinal axis, and spaced from the baffles sufficiently to illuminate the entirety of both sides. Each filter modules comprises a plurality of filters, selected and arranged so as to maximize UV illumination of all filters in the module. For each filter module, the filters are selected from a coarse foam, a fine foam, and a fused quartz felt. Each filter is loaded with a catalyst selected from AEROXIDE® P25, titanium dioxide ($TiO_2$), $TiO_2$ doped with iron ($Fe-TiO_2$), and $TiO_2$ doped with carbon ($C-TiO_2$). The catalysts on the filters, under UV illumination, chemically reduce VOCs in the airflow to non-VOC molecules.

One aspect relates to an aircraft air filtration and volatile organic compound (VOC) removal unit. The VOC removal unit includes an air duct having a longitudinal axis, an air inlet at one end, and air outlet at the other end; a plurality of baffles, each having a plurality of open spaces allowing airflow therethrough, disposed at spaced locations within the duct between the air inlet and outlet, the baffles being generally transverse to the longitudinal axis; a plurality of ultraviolet (UV) light emitting diodes (LED) mounted on each baffle; and a porous and permeable photocatalytic oxidation (PCO) filter module disposed between each pair of baffles, generally transverse to the longitudinal axis, such that air flows through the PCO filter module. Each PCO filter module contains one or more catalysts comprising titanium dioxide ($TiO_2$), $TiO_2$ doped with iron ($Fe-TiO_2$), or $TiO_2$ doped with carbon ($C-TiO_2$) which, when illuminated by UV light, are operative to chemically reduce VOCs to non-VOC molecules.

Another aspect relates to a method of aircraft air filtration and volatile organic compound (VOC) removal. Cabin air is directed to an air inlet of an aircraft air filtration and VOC removal unit comprising an air duct having a longitudinal axis, whereby the air flows through open spaces in a plurality of baffles disposed at spaced locations within the duct and generally transverse to the longitudinal axis, and also through a porous and permeable photocatalytic oxidation (PCO) filter module disposed between each pair of baffles and generally transverse to the longitudinal axis, and then out of an air outlet. The PCO filter modules are illuminated with ultraviolet (UV) light from UV light emitting diodes (LED) mounted on each baffle. Each PCO filter module contains one or more catalysts comprising titanium dioxide ($TiO_2$), $TiO_2$ doped with iron ($Fe-TiO_2$), or $TiO_2$ doped with carbon ($C-TiO_2$) which, when illuminated by UV light, are operative to chemically reduce VOCs to non-VOC molecules.

BRIEF DESCRIPTION OF THE DRAWINGS

The present disclosure will now be described more fully hereinafter with reference to the accompanying drawings, in which aspects of the disclosure are shown. However, this disclosure should not be construed as limited to the aspects set forth herein. Rather, these aspects are provided so that this disclosure will be thorough and complete, and will fully convey the scope of the disclosure to those skilled in the art. Like numbers refer to like elements throughout.

DETAILED DESCRIPTION

For simplicity and illustrative purposes, the present disclosure is described by referring mainly to an exemplary aspect thereof. In the following description, numerous specific details are set forth in order to provide a thorough understanding of the present disclosure. However, it will be readily apparent to one of ordinary skill in the art that the aspects of the present disclosure can be practiced without limitation to these specific details. In this description, well known methods and structures have not been described in detail so as not to unnecessarily obscure the present disclosure.

Figure 1:
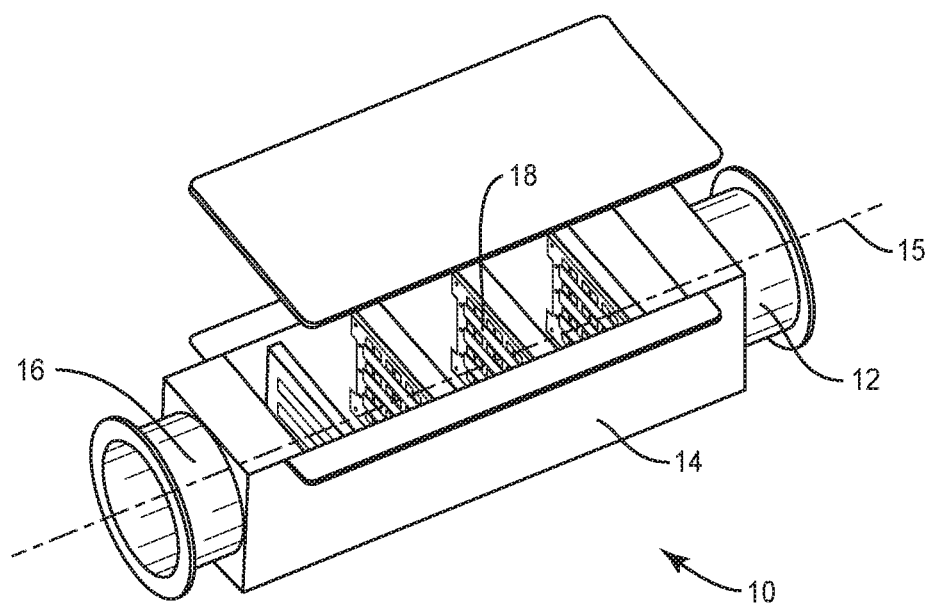
FIG. 1 is a perspective view of an example aircraft air filtration and VOC removal unit.

FIG. 1 depicts an example compact, lightweight, low power aircraft air filtration and VOC removal unit 10 (hereinafter referred to as simply a "VOC removal unit" 10), according to one aspect of the present disclosure. The VOC removal unit 10 operates to remove VOCs from cabin air by photocatalytic oxidation (PCO), as will be explained in greater detail herein. The VOC removal unit 10 is designed specifically for use on an aircraft. Accordingly, it is small and lightweight. The design maximizes airflow through the VOC removal unit 10, and minimizes heat generation and a thermal gradient across it, consistent with the maximum achievable UV illumination of PCO filters. Numerous aspects of component design, placement, and spacing achieve this optimization.

Figure 2:
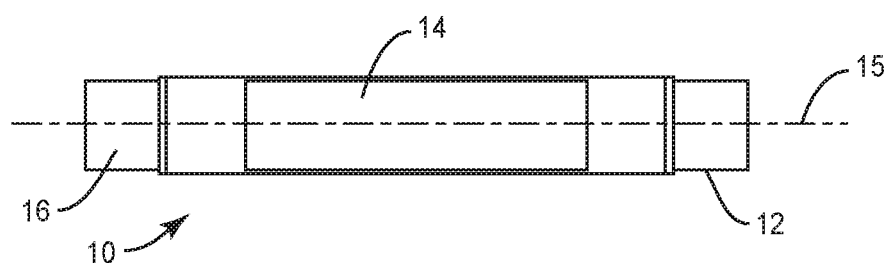
FIG. 2 is a plan view of the example VOC removal unit, showing dimensions according to one aspect.
Figure 3:
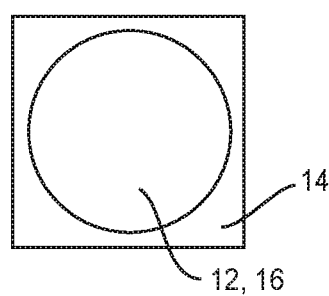
FIG. 3 is a cross-section view of the example VOC removal unit, showing dimensions of the inlet/outlet and duct according to one aspect.

FIG. 1 is a perspective view of an example VOC removal unit 10, with one side removed to reveal internal components. FIGS. 2 and 3 are sections views of the VOC removal unit 10 according to one aspect, and FIG. 5 is a section view showing the spacing and relationship of various components.

The VOC removal unit 10 comprises an air inlet 12, a duct 14 having a longitudinal axis 15, and an air outlet 16. In the representative aspect of the VOC removal unit 10 depicted in the figures, the air inlet 12 and outlet 16 have a circular cross-sectional shape, and the duct 14 has a square cross-section. However, those of skill in the art will readily recognize that other shapes can be utilized, within the scope of the present disclosure.

Figure 5:
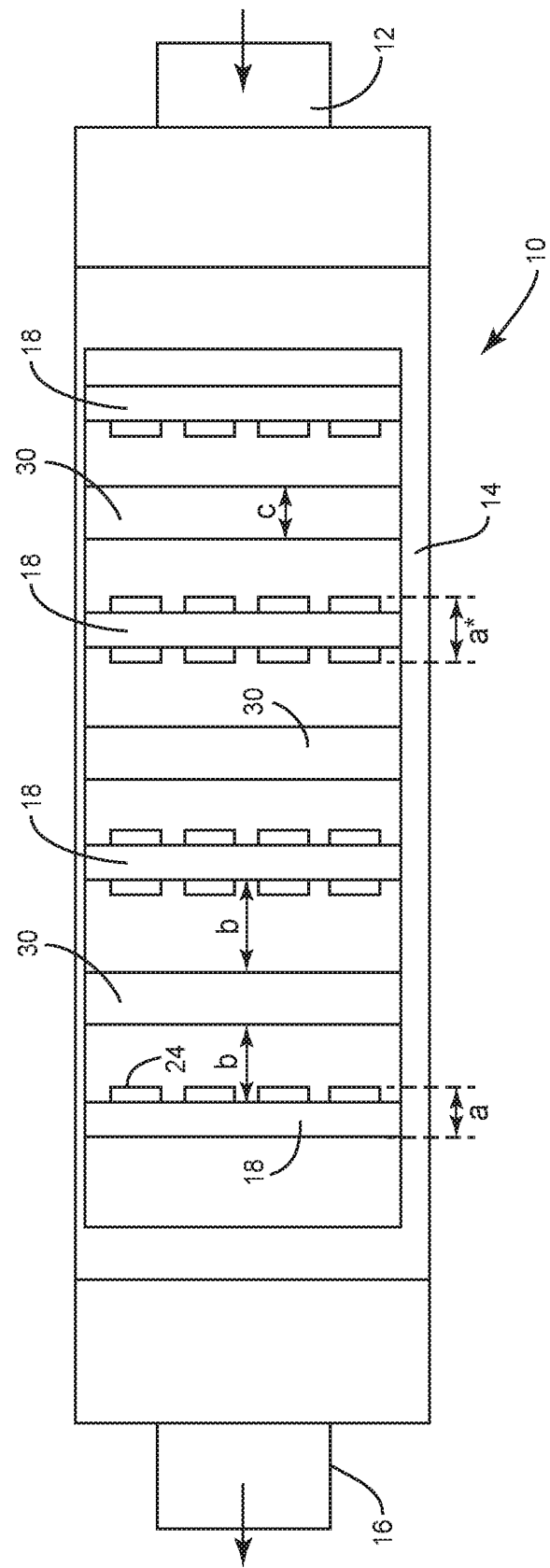
FIG. 5 is a section view of the example VOC removal unit showing the spatial relationship between baffles, UV LEDs, and filter modules.

FIG. 5 depicts the overall operative structure of the VOC removal unit 10. A plurality of baffles 18 is disposed at spaced locations within the duct 14. Between each pair of baffles 18, a PCO filter module 30 comprises a plurality of filters, each of which is loaded with a photoactive catalyst. The number and spacing (as explained further below) of baffles 18 and PCO filter modules 30 is representative. In other aspects, more or fewer of each may be provided. In general, the number of baffles 18 will always exceed the number of PCO filter modules 30 by one—with baffles 18 disposed at both ends and in between each pair of PCO filter modules 30. Ultraviolet (UV) light emitting diodes (LED) 24 mounted on the baffles 18 illuminate both sides of the filter modules 30 with UV light to maximize illumination of photocatalytic coatings on material in the filter modules 30. Since the photocatalytic coatings require UV light as a catalyst to convert VOCs to non-VOC molecules, maximizing the illumination of PCO modules 30 with UV light maximizes the effectiveness of the VOC removal unit 10. Cabin air directed through the VOC removal unit 10 passes through the baffles and PCO filter modules 30. As explained further herein, UV light illuminating the PCO filter modules 30 photoactivates catalysts loaded therein, initiating a chemical photocatalytic oxidation process that reduces VCOs in the air to non-VCO molecules, such as carbon dioxide and water.

Figure 4:
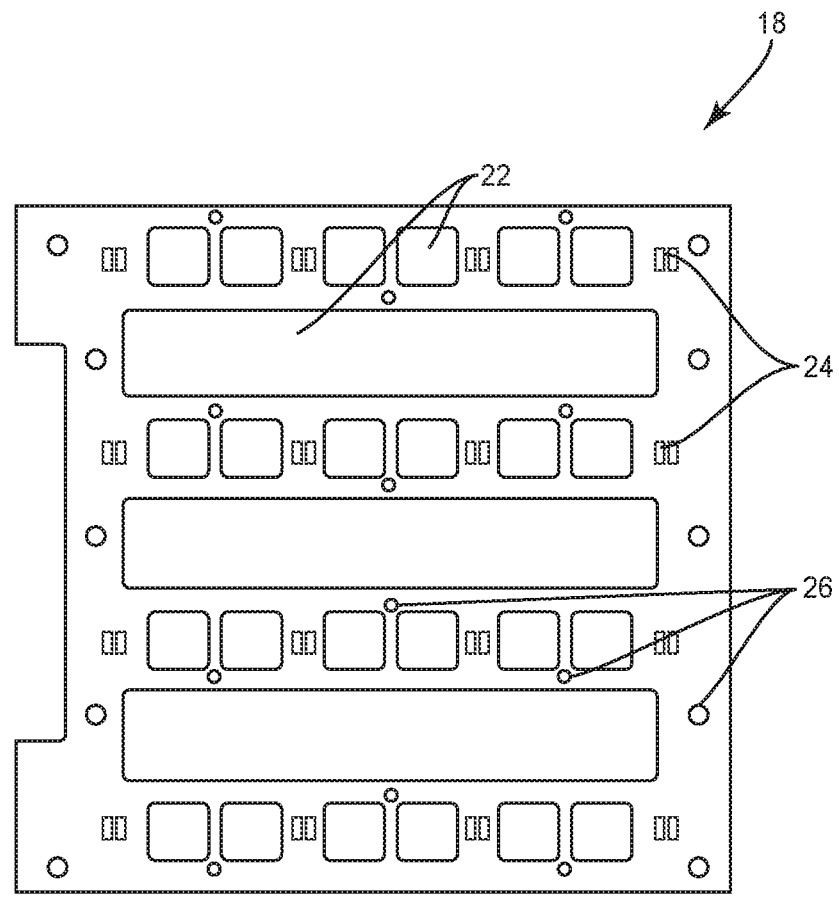
FIG. 4 is a side view of an example baffle.

The baffles 18 are disposed at spaced locations within the duct 14, between the air inlet 12 and air outlet 16. The baffles 18 are disposed generally transverse to the longitudinal axis 15 of the duct 14. As depicted in FIG. 4, each baffle 18 has a plurality of airflow spaces 22 formed in it, allowing airflow therethrough. A plurality of UV LEDs 24 is mounted on each baffle. The UV LEDs 24 are disposed both around the periphery of each baffle 18, and between the airflow spaces 22, so as to maximize the UV illumination of adjacent filter modules 30. The UV LEDs 24 are mounted on the interior sides of baffles 18 adjacent the air inlet 12 and outlet 16, and are mounted on both sides of all other baffles 18, so as to illuminate the filter modules 30 from both sides. Mounting UV LEDs 24 on all baffles 18 ensures maximum illumination of all filter modules 30, for maximum photocatalytic effect.

The efficacy of the VOC removal unit 10 is greatest when the UV LEDs 24 are operated at high power (~500 mA), thus generating a large luminous flux of UV light to activate the photoactive catalysts in the filter modules 30. However, this generates heat, which warms the air flowing through the duct 14, increasing the load on aircraft air conditioning equipment. In one aspect a heat sink is connected to at least one, and preferably to each baffle 18 that includes LEDs 24, using heat sink mounting holes 26. This is done to maintain the life of the UV-LED lights by maintaining lower temperatures on their surface in low flow conditions, prolonging their life. In certain filter configurations (designed for those with higher flow rates) the heat sinks may not be necessary.

A porous and permeable PCO filter module 30, comprising a plurality or "stack" of filters, is disposed between each baffle 18. The PCO filter modules 30 are disposed generally transverse to the longitudinal axis 15 of the duct 14, such that air flows through the PCO filter module 30. Each PCO filter module 30 contains one or more catalysts which, when illuminated by UV light, are operative to chemically reduce VOCs to non-VOC molecules. Maximum UV illumination of all filters in each filter module 30 is thus desired, to maximize the efficacy of VOC removal. Accordingly, the PCO filter modules 30 are spaced apart from the baffles such that the entirety of both surfaces of each PCO filter module is illuminated by UV light.

If a PCO filter module 30 were directly adjacent a baffle 18, only spots on the surface of the PCO filter module 30 that contact a UV LED 24 would be illuminated. As the spacing between the PCO filter module 30 and the baffle 18 increases, the illumination spot sizes grow and the photonic efficiency decreases. The optimal spacing is that distance at which the illumination spots just overlap, fully illuminating the entire facing surface of the PCO filter module 30—increasing the spacing beyond this distance reduces the luminous flux of UV light. In the aspect depicted in FIG. 5, the distance between each face of a filter module 30 and the facing baffle 18 is 20 mm (dimension "b"); at this distance, 500 mA of power applied to the UV LEDs 24 yields a light intensity of over 20 mW/cm$^2$. The filter modules 30 in this aspect are 40 mm thick (dimension "c"). In the aspect depicted, the baffles 18, measured to the outermost protruding UV LEDs 24, are 15 mm thick for those adjacent to the air inlet 12 and outlet 16, which have UV LEDs 24 mounted on only the interior-facing sides (dimension "a"), and 30 mm thick for interior baffles 18, which have UV LEDs 24 mounted on both sides (dimension "a*"). These dimensions are exemplary; those of skill in the art may readily deduce optimal relative spacing of components for VOC removal units of different size or shape.

The filters in each PCO filter module 30 are loaded with some form of titanium dioxide ($TiO_2$). Photocatalytic oxidation occurs in the VOC removal unit 10 by illuminating the $TiO_2$ in the filters with UV light, generating hydroxyl radicals (OH.) by reaction with water molecules in the air. The free radicals, in turn, oxidize VOCs into non-VOC molecules—primarily carbon dioxide ($CO_2$) and water ($H_2O$). These are returned to the aircraft cabin, avoiding the accumulation of contaminants.

Titanium dioxide is a light-sensitive semiconductor, which absorbs electromagnetic radiation in the near UV region. The most common natural form of $TiO_2$ is the mineral rutile. Other forms of $TiO_2$ are anatase (also known as octahedrite) and brookite (an orthorhombic mineral). $TiO_2$, when used as a photoactive catalyst, is primarily anatase, with a small amount of rutile. The anatase form of $TiO_2$ requires higher light energy than the rutile form, but shows a stronger photoactivity. The energy difference between the valence and the conductivity bands of a $TiO_2$ molecule in the solid state is 3.05 eV for rutile and 3.29 eV for anatase, corresponding to a photonic absorption band at <415 nm for rutile and <385 nm for anatase.

Absorption of light energy causes an electron to be promoted from the valence band to the conduction band. This electron, and the simultaneously created positive "electron hole," can move on the surface of the solid, where it can take part in redox reactions. In particular, water molecules in vapor state in the air are adsorbed onto the $TiO_2$ surface where they react with the free electron, generating hydroxyl radicals (OH.). These radicals are uncharged, short-lived, highly reactive forms of hydroxide ions (OH—), bearing considerable oxidizing power. The OH. radicals can cause complete oxidation of organic compounds to carbon dioxide and water. In some aspects, the OH. radicals reduce VOCs to the following end products:

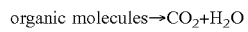
organic molecules→$CO_2$+$H_2O$

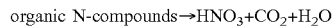
organic N-compounds→$HNO_3$+$CO_2$+$H_2O$

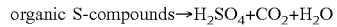
organic S-compounds→$H_2SO_4$+$CO_2$+$H_2O$

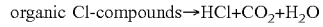
organic Cl-compounds→HCl+$CO_2$+$H_2O$

Although the primary application of photocatalytic oxidation in the VOC removal unit 10 is to reduce VOCs into non-VOC molecules, the process also kills contaminants in bioaerosols, such as bacteria, molds, and fungus. In general, reduction of VOC levels in cabin air enhances comfort of passengers.

The photoactivity of $TiO_2$ is known, and has commercial applications. AEROXIDE® P25 is a nanostructured, fine-particulate pure titanium dioxide with high specific surface area. The product is available from Evonik Industries of Parsippany, N.J. AEROXIDE® P25 is a fine white powder with hydrophilic character caused by hydroxyl groups on the surface. It consists of aggregated primary particles. The aggregates are several hundred nm in size and the primary particles have a mean diameter of approximately 21 nm. The weight ratio of anatase to rutile is approximately 80/20. AEROXIDE® P25 is sold commercially as a photoactive catalyst. With its high purity, high specific surface area, and combination of anatase and rutile crystal structure, AEROXIDE® P25 is widely used for catalytic and photocatalytic applications. Other forms of pure $TiO_2$ may also be used in PCO filter modules 30 in the VOC removal unit 10.

Additionally, the inventors have found that doping $TiO_2$ with iron (Fe—$TiO_2$) and carbon (C—$TiO_2$) yield superior photocatalytic results. The UV-PCO reactor relies on sorption of the organic compounds onto the surface of the catalyst to enable breakdown of the compounds. Doping the $TiO_2$ with carbon or iron increases the sorption capacity of the catalyst, which allows for greater removal of VOCs from the airstream. Through doping with metal and non-metal agents the band gap energy level of $TiO_2$ is lowered and electron-hole pair mechanism is kept constant with a longer duration for higher light absorption capability which results in better efficiency.

Table 1 below lists pre- and post-filtering concentrations of various representative VOCs (i.e., ethanol, or EtOH; acetone; and limonene) for pure $TiO_2$, Fe—$TiO_2$, and C—$TiO_2$, when loaded onto various filter media types. It is clear from these data that Fe—$TiO_2$, and C—$TiO_2$ provide superior VOC removal results, as compared to pure $TiO_2$.

TABLE 1

Relative Performance of Photoactive Catalysts

| Substrate | VOC Type | Initial VOC Concentration (ppb) | Final VOC Concentration (ppb) | Efficiency |
|---|---|---|---|---|
| pure $TiO_2$ | | | | |
| Coarse Foam | EtOH | 423.40 | 350.22 | 17.2% |
| | Acetone | 117.30 | 78.80 | 32.8% |
| Fine Foam | EtOH | NA | NA | NA |
| | Acetone | NA | NA | NA |
| Coarse/Fine Foam | EtOH | 449.00 | 320.20 | 28.6% |
| | Acetone | NA | NA | NA |
| Fe-doped $TiO_2$ | | | | |
| Coarse Foam | EtOH | 389.20 | 198.70 | 48.9% |
| | Acetone | 74.50 | 30.30 | 59.3% |
| Fine Foam | EtOH | NA | NA | NA |
| | Acetone | NA | NA | NA |
| Coarse/Fine Foam | EtOH | 499.30 | 196.70 | 60.6% |
| | Acetoe | NA | NA | NA |
| | Limonene | 39.30 | 9.30 | 68.7% |
| C-doped $TiO_2$ | | | | |
| Coarse Foam | EtOH | NA | NA | NA |
| | Acetone | NA | NA | NA |
| Fine Foam | EtOH | NA | NA | NA |
| | Acetone | NA | NA | NA |
| Coarse/Fine Foam | EtOH | 417.40 | 203.45 | 51.2% |
| | Acetone | 152.30 | 80.90 | 46.8% |

NA: Not Available

The photoactive catalyst—whether AEROXIDE® P25, other pure $TiO_2$, Fe—$TiO_2$, or C—$TiO_2$—is loaded into a porous and air- and light-permeable filter. In one aspect, the photoactive catalyst is adhered to all surface area of the filter, including within pores and passages running throughout the volume of the filter medium. In at least one aspect, the catalyst is deposited by a dip coating method, followed by drying at 80-100° C. Other methods of catalyst deposition may be used.

The type of substrate and coating methods have important effects on coating stability, photocatalytic, and mechanical performance of the filters. Porous metal substrates offer better toughness, better malleability, and lower cost than ceramic substrates. However, using metal substrate generally results in peeling coatings with cracks. This occurs at heating stage and due to difference in thermal expansion coefficients between the $TiO_2$ and the substrate metal.

Porous $TiO_2$ filters are commonly employed to avoid this problem. Such filters are commonly prepared by coating a TiO₂ sol, slurry, or precursor liquid onto ceramic substrates, metal meshes or ceramic or metallic foam by different coating methods. After coating application, heat treatment necessary for photocatalysts activity around 500° C. is generally conducted.

In one aspect, three filter types are used in PCO filter modules 30: coarse foam, fine foam, and fused quartz filament felt. Both the porosity (number and size of pores, or voids) and the permeability (ability of fluid to flow through, which is related to interconnectivity of the pores) of each type of filter type are important. Porosity is important as a large number of pores provide the surface area for adhering more photocatalytic coatings. Permeability is important as a large volume of air must flow through the PCO filter modules 30 to remove VCOs from the cabin air of a large aircraft.

The coarse foam is a relatively open foam, with average pores size of approximately 2540 um, and high permeability. The coarse foam filter is approximately 10 mm thick. A suitable coarse foam is available from Recemat BV of the Netherlands. This material can be uniformly coated with catalyst, and is it fairly easy to coat. The coarse foam filter allows much of the incident UV light to penetrate the foam, thus illuminating successive filters. For this reason, in some aspects, a coarse foam filter is at both exterior positions of a "stack" of filters forming a PCO filter module 30. The position of coarse foam filter is also maintained on the outside of whole filter stack to start the VOC degradation in a lower specific surface area to very high specific surface area in fine foam filters.

The fine foam is a denser foam, with average pores size of approximately 800 um, and lower permeability as compared to coarse foam but with a higher surface area. Accordingly, the fine foam filter is thinner than the coarse foam filter, at approximately 2-4 mm, to maintain robust airflow. This material is more difficult to coat uniformly with catalyst. A suitable fine foam is available from Alantum GMBH of Germany.

Another type of material is made from fused quartz filaments. A suitable felt of this type is QUARTZEL® felt, available from Magento of the USA. The QUARTZEL® felt is difficult to coat uniformly, and presents a high resistance to air flow. Accordingly, it is used sparingly. In one aspect, only one of three PCO filter modules 30 in a VOC removal unit 10 include a fused quartz filament filter, and that module 30 includes only a single such filter.

Each PCO filter module 30 comprises a plurality of catalyst-loaded filters selected and arranged to maximize UV illumination of all of the filters. With, in some aspect, three filter media and four types of photoactive catalysts, there are a dozen combinations of PCO filters from which to select. The number of permutations of which of these filters to stack into a filter module 30, in which order, is very large. Furthermore, different PCO filter modules—that is, different selections and arrangements of photoactive-catalyst-loaded filters—can be placed in different locations along the duct 14 of the VOC removal unit 10. Of these many possibilities, the inventors have discovered and extensively tested a few near-optimal combinations.

In one aspect, as depicted in FIG. 5, an aircraft air filtration and volatile organic compound (VOC) removal unit 10 includes an air duct 14 having a longitudinal axis 15, an air inlet 12 at one end, and air outlet 16 at the other end; a plurality of baffles 18 (FIG. 4), each having a plurality of open spaces 22 allowing airflow therethrough, disposed at spaced locations within the duct 14 between the air inlet 12 and air outlet 16, the baffles 18 being generally transverse to the longitudinal axis 15; a plurality of ultraviolet (UV) light emitting diodes (LED) 24 mounted on each baffle 18; and a porous and permeable photocatalytic oxidation (PCO) filter module 30 disposed between each pair of baffles 18, generally transverse to the longitudinal axis 15, such that air flows through the PCO filter module 30. Each PCO filter module 30 contains one or more catalysts comprising titanium dioxide ($TiO_2$), $TiO_2$ doped with iron (Fe—$TiO_2$), $TiO_2$ doped with carbon (C—$TiO_2$), or combinations thereof, which, when illuminated by UV light, are operative to chemically reduce VOCs to non-VOC molecules. This provides a compact, lightweight, low-power means for removing VOCs, which is suited for aircraft.

In one aspect, the VOC removal unit further includes one or more heat sinks disposed within the duct and adapted to conduct heat away from the UV LEDs away and maintain their lifespan. This prevents overheating of the LEDs to prolong their life in a low flow situation.

In one aspect, the UV LEDs are disposed both around a periphery of each baffle and between the airflow spaces so as to maximize the UV illumination of adjacent PCO filter modules. The UV LEDs are mounted on interior sides of baffles adjacent the air inlet and outlet, and are mounted on both sides of all other baffles, so as to illuminate the PCO filter modules from both sides. The PCO filter modules are spaced apart from the baffles such that the entirety of both surfaces of each PCO filter module is illuminated by UV light. These features ensure maximum and even illumination of the PCO filter modules by UV light.

Each PCO filter module comprises a plurality of filters, each filter selected from the group consisting of a coarse foam, a fine foam, and a fused quartz filament felt, and each filter is loaded with a catalyst which may be one or more of pure titanium dioxide ($TiO_2$), $TiO_2$ doped with iron (Fe—$TiO_2$), and $TiO_2$ doped with carbon (C—$TiO_2$), and combinations thereof. In one aspect, each PCO filter module comprises a plurality of catalyst-loaded filters selected and arranged to maximize UV illumination of all of the filters. These materials have high durability and the arrangements facilitate the removal of VOCs.

The VOC removal unit 10 comprises four baffles 18 and three PCO filter modules 30. The PCO filter modules 30 comprise, in order from air inlet 12 to air outlet 16,
1) R25-CTR-TA-R25;
2) CTR-TA-Q25-R25-R25; and
3) R25-CTR-TA-R25; where
R25 is a coarse foam loaded with pure $TiO_2$;
Q25 is a fused quartz filament felt loaded with pure $TiO_2$;
CTR is a coarse foam loaded with C—$TiO_2$ and
TA is a fine foam loaded with pure $TiO_2$.

In another aspect, with the same numbers of baffles 18 and PCO filter modules 30, the PCO filter modules 30 comprise, in order from air inlet 12 to air outlet 16,
1) R25-TA-FTR-CTR;
2) R25-CTA-FTR-Q25-R25; and
3) R25-TA-FTR-CTR; where
FTR is a coarse foam loaded with Fe—$TiO_2$.

Based on the information disclosed herein, those of skill in the art may devise numerous other selections and arrangements of both photoactive catalyst-loaded filters in each PCO filter module 30, and the PCO filter modules 30 in the VOC removal unit 10, within the scope of the present disclosure.

Figure 6:
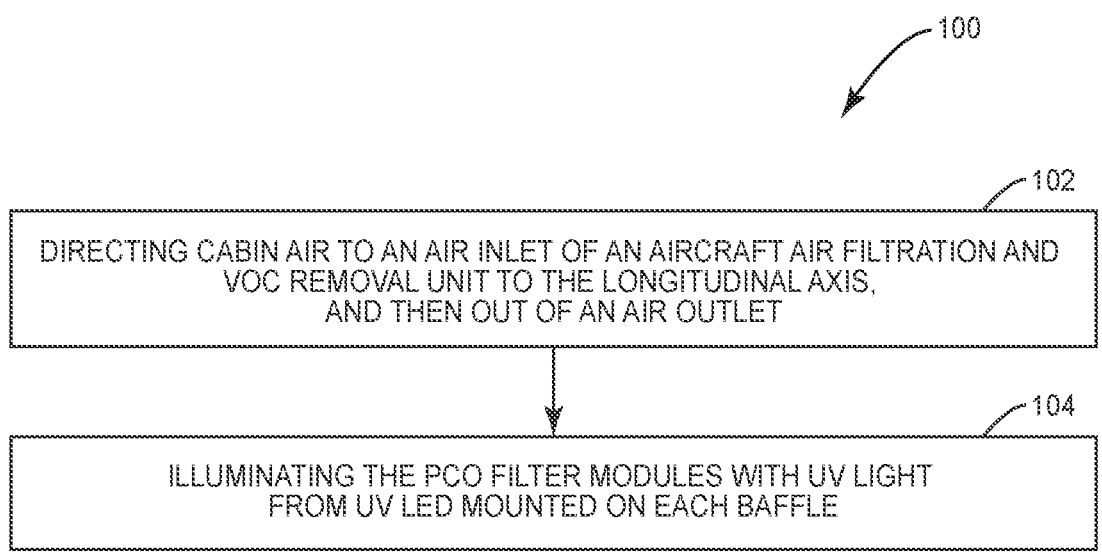
FIG. 6 is a flow diagram of an exemplary method of aircraft air filtration and VOC removal.

FIG. 6 depicts steps in a method 100 of aircraft air filtration and VOC removal. Cabin air is directed to an air inlet 12 of an aircraft air filtration and VOC removal unit 10 comprising an air duct 14 having a longitudinal axis 15, whereby the air flows through airflow spaces 22 in a plurality of baffles 18 disposed at spaced locations within the duct 14 and generally transverse to the longitudinal axis 15, and also through a porous and permeable PCO filter module 30 disposed between each pair of baffles 18 and generally transverse to the longitudinal axis 15, and then out of an air outlet 16 (block 102). The PCO filter modules 30 are illuminated with UV light from UV LEDs 24 mounted on each baffle 18 (block 104). Each PCO filter module 30 contains one or more catalysts comprising titanium dioxide ($TiO_2$), $TiO_2$ doped with iron ($Fe$—$TiO_2$), or $TiO_2$ doped with carbon ($C$—$TiO_2$) which, when illuminated by UV light, are operative to chemically reduce VOCs to non-VOC molecules (block 104). The method 100 allows for VOC removal from cabin air in a compact, lightweight, low-power manner.

The method 100 further comprises conducting heat from the UV LEDs away from the airflow via one or more heat sinks disposed within the duct. This prevents excessive heat build-up in the LEDs in a low airflow system.

The method 100 can include illuminating the PCO filter modules with UV light comprises disposing the UV LEDs both around the periphery of each baffle and between the airflow spaces, so as to maximize the UV illumination of adjacent PCO filter modules. This maximizes the effectiveness of the PCO filter modules 30.

The method 100 can include disposing the UV LEDs on the baffles comprises disposing the UV LEDs on interior sides of baffles adjacent the air inlet and outlet, and on both sides of all other baffles, so as to illuminate the PCO filter modules from both sides. In one aspect of the method 100, illuminating the PCO filter modules with UV light comprises spacing the PCO filter modules apart from the baffles such that the entirety of both surfaces of each PCO filter module is illuminated by UV light. This provides uniform UV illumination of all filter surfaces, maximizing their effectiveness.

In one aspect of the method 100, each PCO filter module comprises one or more filters, each filter selected from the group consisting of a coarse foam, a fine foam, and a fused quartz filament felt, and wherein each filter is loaded with a catalyst which may be one or more of pure titanium dioxide ($TiO_2$), $TiO_2$ doped with iron ($Fe$—$TiO_2$), and $TiO_2$ doped with carbon ($C$—$TiO_2$). These catalysts enhance VOC removal.

The method 100 can include illuminating the PCO filter modules with UV light comprises selecting and arranging a plurality of catalyst-loaded filters to form each PCO filter module so as to maximize UV illumination of all of the filters. In one aspect, the VOC removal unit comprises four baffles and three PCO filter modules, and the PCO filter modules comprise, in order from air inlet to air outlet, 1) R25-CTR-TA-R25; 2) CTR-TA-Q25-R25-R25; and 3) R25-CTR-TA-R25, where R25 is a coarse foam loaded with pure $TiO_2$; Q25 is a fused quartz filament felt loaded with pure $TiO_2$; CTR is a coarse foam loaded with $C$—$TiO_2$ and TA is a fine foam loaded with pure $TiO_2$. In another aspect, the PCO filter modules comprise, in order from air inlet to air outlet, 1) R25-TA-FTR-CTR; 2) R25-CTA-FTR-Q25-R25; and 3) R25-TA-FTR-CTR; where FTR is a coarse foam loaded with Fe—TiO2. These particular selections and arrangements provide good VOC removal performance.

The method 100 further comprises filtering contaminants from the airflow by directing the air through an activated carbon filter. This assists in contaminant removal.

Photocatalytic oxidation is a known effective means of VOC removal. See Stevens, et al., Investigation of the Photocatalytic Oxidation of Low-Level Carbonyl Compounds, *J. Air Waste Manag. Assoc.* 1998 October; 48(10): 979-984 ("PCO of the formaldehyde and acetone was nearly 100% for all reactor designs."). See also, Hodgson, et al., Performance of ultraviolet photocatalytic oxidation for indoor air cleaning applications, *Indoor Air* 2007; 17: 305-316 (conversion rate of 80% for 27 VOCs characteristic of office buildings and 10 VOCs emitted by cleaning products). These implementations were generally large, heavy, and utilized large amounts of power, primarily to drive banks of UV lamps. By utilizing UV LEDs 24 illuminating both sides of PCO filter modules 30 designed to transmit the UV light deep into the PCO filter modules 30 to illuminate, and thus photoactivate, catalysts loaded therein, the VOC removal unit 10 provides a compact, lightweight, low-power implementation of photocatalytic oxidation, allowing for its use on aircraft.

The present disclosure can, of course, be carried out in other ways than those specifically set forth herein without departing from essential characteristics of the disclosure. The present aspects are to be considered in all respects as illustrative and not restrictive, and all changes coming within the meaning and equivalency range of the appended claims are intended to be embraced therein.

What is claimed is:

1. An aircraft air filtration and volatile organic compound (VOC) removal unit, comprising:
   an air duct having a longitudinal axis, an air inlet at one end, and air outlet at the other end;
   a plurality of baffles, each having a plurality of airflow spaces allowing airflow therethrough, disposed at spaced locations within the duct between the air inlet and air outlet, the baffles being generally transverse to the longitudinal axis;
   a plurality of ultraviolet (UV) light emitting diodes (LED) mounted on each baffle; and
   a porous and permeable photocatalytic oxidation (PCO) filter module disposed between each pair of baffles, generally transverse to the longitudinal axis, such that air flows through the PCO filter module;
   wherein each PCO filter module contains one or more catalysts comprising titanium dioxide ($TiO_2$), $TiO_2$ doped with iron ($Fe$—$TiO_2$), $TiO_2$ doped with carbon ($C$—$TiO_2$), or combinations thereof which, when illuminated by UV light, are operative to chemically reduce VOCs to non-VOC molecules;
   wherein each PCO filter module comprises a plurality of filters, each of the plurality of filters including one or more of a coarse foam, a fine foam, a fused quartz filament felt, or combination thereof, and wherein each of the plurality of filters is loaded with a catalyst including one or more of pure titanium dioxide ($TiO_2$), $TiO_2$ doped with iron ($Fe$—$TiO_2$), $TiO_2$ doped with carbon ($C$—$TiO_2$), or combination thereof;
   wherein the VOC removal unit comprises four baffles and three PCO filter modules, and
   wherein the PCO filter modules comprise, in order from air inlet to air outlet,
   1) R25-CTR-TA-R25;
   2) CTR-TA-Q25-R25-R25; and
   3) R25-CTR-TA-R25, where
   R25 is a coarse foam loaded with pure $TiO_2$;
   Q25 is a fused quartz filament felt loaded with pure $TiO_2$;
   CTR is a coarse foam loaded with $C$—$TiO_2$ and
   TA is a fine foam loaded with pure $TiO_2$.

2. The VOC removal unit of claim 1 further comprising one or more heat sinks disposed within the duct and adapted to conduct heat away from the UV LEDs to prolong their lifespan.

3. The VOC removal unit of claim 1 wherein the UV LEDs are disposed both around a periphery of each baffle and between the airflow spaces so as to maximize UV illumination of an adjacent PCO filter module.

4. The VOC removal unit of claim 3 wherein UV LEDs are mounted on interior sides of baffles adjacent the air inlet and outlet, and are mounted on both sides of all other baffles, so as to illuminate each PCO filter module from both sides.

5. The VOC removal unit of claim 4 wherein the PCO filter module is spaced apart from the baffles such that all of both surfaces of each PCO filter module is illuminated by UV light.

6. The VOC removal unit of claim 1 wherein each PCO filter module comprises a plurality of catalyst-loaded filters selected and arranged to maximize UV illumination of the plurality of catalyst-loaded filters and through a complete depth of each filter layer of the plurality of catalyst-loaded filters.

7. An aircraft air filtration and volatile organic compound (VOC) removal unit, comprising:
   an air duct having a longitudinal axis, an air inlet at one end, and air outlet at the other end;
   a plurality of baffles, each having a plurality of airflow spaces allowing airflow therethrough, disposed at spaced locations within the duct between the air inlet and air outlet, the baffles being generally transverse to the longitudinal axis;
   a plurality of ultraviolet (UV) light emitting diodes (LED) mounted on each baffle; and
   a porous and permeable photocatalytic oxidation (PCO) filter module disposed between each pair of baffles, generally transverse to the longitudinal axis, such that air flows through the PCO filter module;
   wherein each PCO filter module contains one or more catalysts comprising titanium dioxide ($TiO_2$), $TiO_2$ doped with iron ($Fe-TiO_2$), $TiO_2$ doped with carbon ($C-TiO_2$), or combinations thereof which, when illuminated by UV light, are operative to chemically reduce VOCs to non-VOC molecules;
   wherein each PCO filter module comprises a plurality of filters, each of the plurality of filters including one or more of a coarse foam, a fine foam, a fused quartz filament felt, or combination thereof, and wherein each filter is loaded with a catalyst including one or more of pure titanium dioxide ($TiO_2$), $TiO_2$ doped with iron ($Fe-TiO_2$), $TiO_2$ doped with carbon ($C-TiO_2$), or combination thereof
   wherein the VOC removal unit comprises four baffles and three PCO filter modules; and
   wherein the PCO filter modules comprise, in order from air inlet to air outlet,
   1) R25-TA-FTR-CTR;
   2) R25-CTA-FTR-Q25-R25; and
   3) R25-TA-FTR-CTR; where
   R25 is a coarse foam loaded with pure $TiO_2$;
   Q25 is a fused quartz filament felt loaded with pure $TiO_2$;
   CTR is a coarse foam loaded with $C-TiO_2$;
   TA is a fine foam loaded with pure $TiO_2$; and
   FTR is a coarse foam loaded with $Fe-TiO_2$.

8. The VOC removal unit of claim 7 further comprising one or more heat sinks disposed within the duct and adapted to conduct heat away from the UV LEDs to prolong their lifespan.

9. The VOC removal unit of claim 7 wherein the UV LEDs are disposed both around a periphery of each baffle and between the airflow spaces so as to maximize UV illumination of an adjacent PCO filter module.

10. The VOC removal unit of claim 7 wherein each PCO filter module comprises a plurality of catalyst-loaded filters selected and arranged to maximize UV illumination of the plurality of catalyst-loaded filters and through a complete depth of each filter layer of the plurality of catalyst-loaded filters.

11. A method of aircraft air filtration and volatile organic compound (VOC) removal, comprising:
   directing cabin air to an air inlet of an aircraft air filtration and VOC removal unit comprising an air duct having a longitudinal axis, whereby the air flows through airflow spaces in a plurality of baffles disposed at spaced locations within the duct and generally transverse to the longitudinal axis, and also through a porous and permeable photocatalytic oxidation (PCO) filter module disposed between each pair of baffles and generally transverse to the longitudinal axis, and then out of an air outlet; and
   Illuminating the PCO filter modules with ultraviolet (UV) light from UV light emitting diodes (LED) mounted on each baffle;
   wherein each PCO filter module contains one or more catalysts comprising titanium dioxide ($TiO_2$), $TiO_2$ doped with iron ($Fe-TiO_2$), or $TiO_2$ doped with carbon ($C-TiO_2$) which, when illuminated by UV light, are operative to chemically reduce VOCs to non-VOC molecules;
   wherein each PCO filter module comprises one or more filters, each of the one or more filters including one or more of a coarse foam, a fine foam, a fused quartz filament felt, and combinations thereof, and wherein each of the one or more filters is loaded with a catalyst including one or more of pure titanium dioxide ($TiO_2$), $TiO_2$ doped with iron ($Fe-TiO_2$), $TiO_2$ doped with carbon ($C-TiO_2$), and combinations thereof;
   wherein the VOC removal unit comprises four baffles and three PCO filter modules, and
   wherein the PCO filter modules comprise, in order from air inlet to air outlet,
   1) R25-CTR-TA-R25;
   2) CTR-TA-Q25-R25-R25; and
   3) R25-CTR-TA-R25, where
   R25 is a coarse foam loaded with pure $TiO_2$;
   Q25 is a fused quartz filament felt loaded with pure $TiO_2$;
   CTR is a coarse foam loaded with $C-TiO_2$ and
   TA is a fine foam loaded with pure $TiO_2$.

12. The method of claim 11 further comprising conducting heat from the UV LEDs away from the LEDs via one or more heat sinks disposed within the duct.

13. The method of claim 11 wherein illuminating the PCO filter modules with UV light comprises disposing the UV LEDs both around a periphery of each baffle and between the airflow spaces, so as to maximize the UV illumination of adjacent PCO filter modules.

14. The method of claim 13 wherein disposing the UV LEDs on the baffles comprises disposing the UV LEDs on interior sides of baffles adjacent the air inlet and outlet, and on both sides of all other baffles, so as to illuminate each PCO filter module from both sides.

15. The method of claim 14 wherein illuminating each PCO filter module with UV light comprises spacing each PCO filter module apart from the baffles such that an entirety of both surfaces of each PCO filter module is illuminated by UV light.

16. The method of claim 11 wherein illuminating the PCO filter modules with UV light comprises selecting and arranging a plurality of catalyst-loaded filters to form each PCO filter module so as to maximize UV illumination of all of the filters.

17. A method of aircraft air filtration and volatile organic compound (VOC) removal, comprising:
 directing cabin air to an air inlet of an aircraft air filtration and VOC removal unit comprising an air duct having a longitudinal axis, whereby the air flows through airflow spaces in a plurality of baffles disposed at spaced locations within the duct and generally transverse to the longitudinal axis, and also through a porous and permeable photocatalytic oxidation (PCO) filter module disposed between each pair of baffles and generally transverse to the longitudinal axis, and then out of an air outlet and
 Illuminating the PCO filter modules with ultraviolet (UV) light from UV light emitting diodes (LED) mounted on each baffle;
 wherein each PCO filter module contains one or more catalysts comprising titanium dioxide ($TiO_2$), $TiO_2$ doped with iron ($Fe-TiO_2$), or $TiO_2$ doped with carbon ($C-TiO_2$) which, when illuminated by UV light, are operative to chemically reduce VOCs to non-VOC molecules;
 wherein each PCO filter module comprises one or more filters, each of the one or more filters including one or more of a coarse foam, a fine foam, a fused quartz filament felt, and combinations thereof, and wherein each of the one or more filters is loaded with a catalyst including one or more of pure titanium dioxide ($TiO_2$), $TiO_2$ doped with iron ($Fe-TiO_2$), $TiO_2$ doped with carbon ($C-TiO_2$), and combinations thereof;
 wherein the VOC removal unit comprises four baffles and three PCO filter modules, and
 wherein the PCO filter modules comprise, in order from air inlet to air outlet,
 1) R25-TA-FTR-CTR;
 2) R25-CTA-FTR-Q25-R25; and
 3) R25-TA-FTR-CTR; where
 R25 is a coarse foam loaded with pure $TiO_2$;
 Q25 is a fused quartz filament felt loaded with pure $TiO_2$;
 CTR is a coarse foam loaded with $C-TiO_2$;
 TA is a fine foam loaded with pure $TiO_2$; and
 FTR is a coarse foam loaded with $Fe-TiO_2$.

18. The method of claim 17 further comprising conducting heat from the UV LEDs away from the LEDs via one or more heat sinks disposed within the duct.

19. The method of claim 17 wherein illuminating the PCO filter modules with UV light comprises disposing the UV LEDs both around a periphery of each baffle and between the airflow spaces, so as to maximize the UV illumination of adjacent PCO filter modules.

20. The method of claim 17 wherein illuminating the PCO filter modules with UV light comprises selecting and arranging a plurality of catalyst-loaded filters to form each PCO filter module so as to maximize UV illumination of all of the filters.

\* \* \* \* \*